United States Patent [19]

Kawam et al.

[11] Patent Number: 4,987,243
[45] Date of Patent: Jan. 22, 1991

[54] NOVEL ANTIPERSPIRANT ADDUCT COMPOSITIONS AND PROCESS FOR MAKING SAME

[75] Inventors: Antoine Kawam, Washington, D.C.; Shu-Sen Lee, Olney; Harvey A. Lazar, Silver Spring, both of Md.

[73] Assignee: The Gillette Company, Boston, Mass.

[21] Appl. No.: 324,104

[22] Filed: Mar. 16, 1989

[51] Int. Cl.$^5$ ................................................. C07F 5/06
[52] U.S. Cl. ........................................ 556/27; 556/171
[58] Field of Search ................... 556/2, 171, 186, 170, 556/271; 424/65

[56] References Cited

U.S. PATENT DOCUMENTS

| | | | |
|---|---|---|---|
| 3,792,068 | 2/1974 | Luedders et al. | 556/27 |
| 3,968,203 | 7/1976 | Spitzer et al. | 424/47 |
| 4,331,609 | 5/1982 | Orr | 556/27 |
| 4,606,915 | 8/1986 | Rosenberg et al. | 556/27 X |
| 4,781,917 | 11/1988 | Luebbe et al. | 424/65 |

OTHER PUBLICATIONS

Markovic et al, "Structural and Dynamic Features of Concentrated Non-Aqueous Dispersions", *Colloids and Surfaces*, 24 (1987), 69–82.
Markovic et al, "Small Angle Neutron Scattering Studies on Non-Aqueous Dispersions of Calcium Carbonate", *Colloid and Polymer Science*, 262 (1984), 648–656.
Mates et al, "Steric Stability of Alkoxy-Precipitated $TiO_2$ in Alcohol Solutions", *Colloids and Surfaces*, 24 (1987), 299–313.
CTFA Cosmetic Dictionary, Monographs, 193, defining Oleth-10.
Technical Bulletin for Macol Nonionic Surfactants, Aug. 1985, 1–5.
Technical Bulletin for Volpo Surfactants, date unknown, 1–8.

*Primary Examiner*—Arthur C. Prescott
*Attorney, Agent, or Firm*—Burns, Doane, Swecker & Mathis

[57] ABSTRACT

A process for preparing a submicron antiperspirant adduct. The process begins by dissolving a mixture of an aluminum-containing salt and a steric stabilizer in a solvent. The antiperspirant salt is then precipitated into the steric stabilizer. The resulting adduct of submicron size can be dispersed into a cosmetic carrier or otherwise processed.

18 Claims, No Drawings

NOVEL ANTIPERSPIRANT ADDUCT COMPOSITIONS AND PROCESS FOR MAKING SAME

BACKGROUND OF THE INVENTION

The present invention relates to adducts for use in antiperspirants, and processes for making and using such adducts.

Various antiperspirant formulations are well known in the cosmetic art. Certain ingredients of the formulation will always be present, while others will depend upon the particular form of the antiperspirant, e.g., a stick, a gel, a lotion, or an aerosol. For example, sticks often contain an organic liquid carrier, a gelling agent that provides the antiperspirant stick with its solid character, and an active antiperspirant ingredient. Antiperspirants are applied to an area of the body such as the axilla by rubbing to deposit a layer of antiperspirant. Accordingly, it is desirable that the ingredients used in any antiperspirant formulation result in an antiperspirant which is smooth, non-greasy and non-tacky.

Certain disadvantages exist with current formulations including the fact that a white chalky residue is often left on the body and transferred to clothing, and that the formulation can break down after storage, e.g., a stick can shrink or become flaky and crumbly. A chalky residue after use of a stick antiperspirant is due in part to the fact that relatively large particles of the antiperspirant salt are employed in stick antiperspirants. Since the original stick itself is white, the deposit on the skin is also white.

Accordingly, it would be desirable to produce antiperspirants which are transparent or translucent as well as having the other desirable properties for an antiperspirant. One factor which determines the optical appearance of a dispersion formulation is the particle size of any ingredient which is present in solid form.

The question of the effect of particle size upon optical appearance has been investigated by the paint industry. To develop hiding power, a pigment must be subdivided until the refractions, diffractions, and reflections produced by the many tiny particles are capable of reversing the direction of light rays which strike the particles. The smaller the particle diameter, the greater the number of individual particles in any specified weight or volume, and consequently, the greater the number of pigment interfaces to interfere with the linear transmission of light. Thus, it might be expected that a pigment manufacturer would strive for the smallest possible particle size to obtain the greatest possible hiding power. However, it is also known that a particle disappears optically when its size has been sufficiently reduced.

Studies have shown that the ability of a particle of any given material to scatter or to diffuse light of a particular wavelength is a function of its particle size relative to that wavelength. Various estimates have placed the most effective particle diameter for hiding power at approximately one-half the wavelength of the light involved. Therefore, as the diameter of a pigment particle becomes increasingly smaller than one-half of the shortest wavelength of visible light, about 4,000 angstroms for violet, it begins to disappear because it loses its ability to produce visible interference with the passage of light waves.

However, in the case of particles to be used in antiperspirant products, additional considerations must be taken into account when estimating the optimum antiperspirant particle size needed to achieve clarity. Particle size and particle population or concentration must be carefully balanced. Since antiperspirant compositions require a very high concentration of active ingredients as compared to the model systems described in the colloid scientific literature, the particle sizes to obtain optical clarity must not exceed about 0.20 micron and preferably 0.10 micron.

Unfortunately, when such small particle sizes are used, other factors become important, such as how to prevent such small particles from agglomerating to reform larger particles that could no longer be suited for clear colloidal dispersions. While this area has been the subject of a sizable amount of research, little success has been achieved and only very few substances have been successfully made into stable colloidal dispersions. For example, Markovic et al, "Structural and Dynamic Features of Concentrated Non-Aqueous Dispersions", *Colloids and Surfaces,* 24 (1987), 69–82, and "Small Angle Neutron Scattering Studies on Non-Aqueous Dispersions of Calcium Carbonate", *Colloid and Polymer Science,* 262 (1984), 648–656, describe colloidal dispersions of calcium carbonate in toluene. The core particles of calcium carbonate are stabilized by an adsorbed layer of an alkyl aryl sulfonic acid.

Another study of this effect is an article by Mates et al, "Steric Stability of Alkoxy-Precipitated $TiO_2$ in Alcohol Solutions", *Colloids and Surfaces,* 24 (1987), 299–313. That particular study was an experimental program which evaluated the suitability of various surfactants as steric stabilizers for ethanol suspensions of alkoxy-precipitated $TiO_2$ particles. The purpose of the study was to determine the most suitable surfactants for preventing agglomeration and/or aggregation of the $TiO_2$ particles.

Before proceeding further, a definition of terms used in fine particle size technology is in order. A particle is defined as a single unit of material which can be clearly discerned in a fine particle system either by direct observation or by light or electron microscopes.

Individual particles may be associated into agglomerates or aggregates. Particles in an agglomerate are only loosely associated while in an aggregate, the particles are held together strongly to form a ball or block that acts as a distinct particle for all practical purposes. Therefore, an agglomerate is a loose confederation of particles that can change when it is handled, whereas an aggregate is a strongly welded assembly of particles that will maintain its group identity under normal handling conditions.

A large number of particles, either agglomerated or aggregated or both, is said to constitute a powder. Generally a powder is regarded as being constituted of particles in the size range of approximately 0.1 to 1,000 microns.

Particles less than 0.1 micron are normally dispersed in a vehicle and regarded as constituting a colloidal dispersion. If the vehicle is organic, the dispersion is referred to as an organosol. In the dispersions covered by this invention, stability with the total absence of flocs is mandatory. Flocs are clusters of low-strength agglomerates and aggregates loosely attached to each other by Van der Waals forces.

The behavior of a powder system is determined by surface, inertial, gravitational, and other macroscopic forces. In a colloid, surface energy, capillary attraction, and surface charges very frequently dominate the behavior of the system.

Also, binding forces between particles start assuming considerable proportions as particle size decreases. This is an extremely important consideration when one wishes to attain optical clarity by means of particle size reduction because one must divide the antiperspirant salt to ultrafine size of 0.2 and preferably 0.1 micron or less, suspend the particles in a vehicle, and keep the particles from regrouping to form agglomerates, aggregates, and flocs despite the extremely high particle-to-particle adhesion energies that develop. Furthermore, an ultrafine particle formed by any technique must never be allowed to combine with a sister particle to form the various clusters as previously cited. Thus a particle must be stabilized immediately as it is formed by surrounding it with a protective layer or shell to shield it from contact with another particle during collision. Thus, one must not only reduce the particles to an appropriate size, but must also stabilize those particles.

Finally, two types of colloidal systems exist, viz: sols and gels. A sol consists of discrete, separate particles (normally solids) dispersed in a continuous phase (normally, though not necessarily, a liquid) and resembles a solution in many respects. A gel, however, comprises two continuous phases with one of them normally being a solid.

Accordingly, a need exists for a sol (organosol) of an antiperspirant salt in a cosmetic organic liquid (e.g., an emollient or moisturizer) which is stable during storage even though it is made up of ultrafine particles. A need also exists for an antiperspirant salt in particle sizes sufficiently small to be below the wavelength of light, i.e., substantially below 0.4 microns, thereby resulting in transparency at high concentration. Moreover, a need exists for a method for preparing such particles such that the particle size distribution initially produced, and the distribution maintained over a period of time, are sufficiently uniform that the organosol retains its original transparency or translucency.

SUMMARY OF THE INVENTION

The present invention is a process for preparing a submicron antiperspirant adduct. The process begins by dissolving a mixture of an aluminum-containing antiperspirant salt and a steric stabilizer in a solvent. The antiperspirant salt is then precipitated into the steric stabilizer.

The resulting material is a unique and novel adduct of submicron size which can be dispersed into a cosmetic carrier or otherwise processed.

DETAILED DESCRIPTION OF THE INVENTION

The present invention is a process for preparing a submicron antiperspirant adduct. Essentially, the process precipitates particles of antiperspirant salt in submicron size, and as a part of the precipitation, forms a protective shell of specific materials around each particle to prevent agglomeration; this allows the particle to remain intact when the adduct is dispersed into a vehicle, thus forming a stable dispersion. The material which forms a shell around the product is referred to herein as a "steric stabilizer". One way to achieve steric stabilization involves the use of a material which has two ends, one of which has affinity and compatibility with the surface of the particle to be coated, and the other of which is compatible with the vehicle used to prepare the dispersion.

The process used in this approach to obtain appropriate sized particles is precipitation. The basic substance from which ultrafine particles are desired, and the steric stabilizer, are dissolved in a suitable solvent system, and then the basic substance is precipitated into the steric stabilizer. One means of accomplishing this result is to cause precipitation by removal of the solvent, such as by evaporation of the solvent to precipitate the original substance, or by freeze drying when the solvent is aqueous. In another embodiment which can be employed in certain instances, precipitation of the original substance into the stabilizer can be accomplished by addition of other materials to modify the solubility parameter of the solvent system, followed by separation of the precipitate for further processing.

Essentially, the antiperspirant particle is precipitated immediately as formed into an oriented layer of molecules of the steric stabilizer, which layer surrounds the particle at all times to prevent clustering during collision. This layer of steric stabilizer is attached to the surface of the antiperspirant particle by simple physical adsorption.

Stabilizers for use in the present invention must have well balanced properties to exhibit compatibility with both components of the organosol of the polar antiperspirant and the much less polar or nonpolar delivery vehicle. Typical vehicles are esters such as isopropyl palmitate, or volatile silicones. Hence the ideal stabilizer is a molecule having two moieties: one moiety highly compatible with the polar antiperspirant and the other moiety compatible with a vehicle which is much less polar (an emollient ester) or non-polar (a volatile silicone).

Those skilled in the art will recognize that various materials meet the above criteria. Preferred materials are nonionic surfactants. Suitable nonionic surfactants are ones in which the hydrophilic moiety is chemically compatible with the antiperspirant salt, while the lipophilic moiety is chemically compatible with the cosmetic carrier into which it is formulated. Typical nonionic surfactants for use in the present invention are ethoxylated alcohols, polyethoxylated alcohols, alkyl phenol ethoxylates, sucrose esters, etc. The best results have been obtained with ethoxylated fatty alcohols, i.e., surfactants derived by extending fatty alcohols with various levels of ethylene oxides. Many of the materials are commercially available and of approved cosmetic grade and purity, e.g., stearyl, oleyl, and cetyl alcohols extended with five to forty moles of various alkylene oxides.

A surfactant which has been found to provide excellent properties is Oleth-10 which is the polyethylene glycol ether of oleyl alcohol that conforms to the formula:

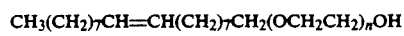

$$CH_3(CH_2)_7CH=CH(CH_2)_7CH_2(OCH_2CH_2)_nOH$$

where n has an average value of 10. This material is available commercially from numerous sources as shown in the Cosmetic Ingredient Dictionary of the CTFA, including under the trademarks MACOL OA-10 (Mazer Chemicals, Inc.; Gurnee, Ill.) and VOLPO 10 (Croda, Inc.; New York, N.Y.).

Suitable alkyl phenol ethoxylates include nonoxynol-8 and octoxynol-9 (CTFA listed). A suitable sucrose ester is sucrose stearate.

As discussed above, in this technique the antiperspirant salt and the steric stabilizer are both dissolved in a common solvent followed by precipitation to leave the antiperspirant salt encapsulated in this steric stabilizer which will remain in the final formulation of the antiperspirant.

Suitable solvents for the antiperspirant salt include water, alcohols, and combinations thereof. A preferred solvent is ethanol because it is readily removed by evaporation to precipitate the antiperspirant particles.

The ratio of stabilizer to salt only becomes important when a clear dispersion based upon particle size is desired. Otherwise, the lower limit for the stabilizer is a sufficient amount for a stable adduct to form, i.e., an amount sufficient to inhibit agglomeration, typically a stabilizer to salt ratio of about 0.1:1, and the upper limit is based upon the desired concentration of salt in the antiperspirant product, a typical maximum being about 3.0:1. It is desirable to minimize the ratio of stabilizer to antiperspirant to ensure a high concentration of actives and a low concentration of additives in the end product. Even if a small particle size is not desired, the present process is advantageous because it provides high purity salt particles free from the decomposition products (like opaque aluminum oxide) obtained during the spray drying process. The conventional process of making antiperspirant salts uses spray drying; the elevated temperatures of this process cause some decomposition of the salt to produce small amounts of an opaque material which is believed to be aluminum oxide.

If a substantially clear dispersion is desired, then the minimum amount of stabilizer becomes important because a sufficient amount must be used to stop crystal growth at the desired size range, i.e., less than about 0.2 microns. In this circumstance the broadest range of stabilizer to salt is 0.5:1 to 3.0:1. The preferred range is 0.75:1 to 2.5:1. A more preferred range is 1:1 to 2.25:1. The most preferred range is 1.25:1 to 1.75:1.

The adduct thus prepared is dispersed into a cosmetic vehicle such as emollient esters, e.g., isopropyl palmitate or isopropyl myristate without the need of a dispersing agent. In this case the stabilizer selected is also an effective dispersing agent because of the high affinity of a part of its molecule to the vehicle. If desired, up to about half of such esters can be replaced with a non-polar silicone fluid such as cyclomethicone without upsetting the compatibility of vehicle and stabilizer.

Clear dispersions from the above adducts can be prepared without additional dispersing agents as is usually required since the steric stabilizers are good dispersing agents; however, it was found that small amounts of water are needed to produce the ultimate dispersion. The minimum amount of water is that sufficient to provide the desired degree of transparency, with the maximum amount of water being less than that which would dissolve the antiperspirant salt. Typically, the water will be between about 2% and about 7% by volume, more preferably about 3-4% by volume.

While not wishing to be bound by theory, it is believed that something more than just particle size is involved in the transparency obtainable by the present invention. For one thing, a considerably higher ratio of surfactant is used than is employed in other systems, and for another, the dispersed adduct remains cloudy until water has been added. Accordingly, there appears to be a relationship between the water and the stabilizer/antiperspirant salt adduct, in addition to the relationship between antiperspirant and stabilizer.

Substantially clear antiperspirant dispersions are defined in the present invention as follows: a dispersion of antiperspirant is substantially clear if its % transmission at 515 nanometers is about 25 or more (% transmission may be measured spectrophotometrically using a 515 nanometer monochromatic beam of radiation and a specimen thickness of two centimeters).

The antiperspirant component used in the present invention may be any of those which contain aluminum, either alone or in combination with other materials such as zirconium. Typical aluminum salts, although not all-inclusive, include:
Aluminum chlorohydrate;
Aluminum sesquichlorohydrate;
Aluminum dichlorohydrate;
Aluminum chlorohydrex PG or PEG;
Aluminum sesquichlorohydrex PG or PEG;
Aluminum dichlorohydrex PG or PEG;
Aluminum zirconium trichlorohydrate;
Aluminum zirconium tetrachlorohydrate;
Aluminum zirconium tetrachlorohydrex PG or PEG;
Aluminum zirconium pentachlorohydrate;
Aluminum zirconium octachlorohydrate;
Aluminum zirconium trichlorohydrex-gly;
Aluminum zirconium tetrachlorohydrex-gly;
Aluminum zirconium pentachlorohydrex-gly
Aluminum zirconium octachlorohydrex-gly;
Aluminum zirconium chloride;
Aluminum zirconium sulfate;
Potassium aluminum sulfate;
Sodium aluminum chlorohydroxylactate;
Aluminum bromohydrate.

In general the active antiperspirant component should be present in the same amounts at which such materials are employed in prior art compositions. As a general rule, the antiperspirant composition should contain from about 5% to about 30%, preferably from about 10 to 25% of the active antiperspirant salt component.

A variety of liquid carriers are suitable for use: examples include isopropyl palmitate; isopropyl myristate; phenyl silicone fluid; and cyclomethicone. The liquid carrier can also contain fragrances and coloring agents as normally used in the art.

The amount of liquid carrier used should be sufficient to provide a suspension of the active antiperspirant ingredient; there is no upper limit of the amount of liquid carrier used, other than the need to have the necessary amount of active component. In general, the antiperspirant should contain from about 40% to about 80% liquid carrier by weight.

For stick antiperspirants, it is necessary to use some gelling agent in the antiperspirant. Suitable gelling agents are well known to those skilled in the art.

In order to further illustrate the present invention and the advantages thereof, the following specific examples are given, it being understood that these examples are intended only to be illustrative without serving as a limitation on the scope of the present invention.

EXAMPLES

The following is a general procedure for the precipitation of an antiperspirant salt into a steric stabilizer via evaporation from an alcoholic solution, and its dispersion into a cosmetic carrier, such as isopropyl palmitate (IPP). A 50% solution of the antiperspirant salt, such as Rehydrol II ™ (aluminum chlorohydrex PG), in 190 proof ethanol with the steric stabilizer at the desired ratio of steric stabilizer: antiperspirant salt is added to a preweighed round bottom flask. The flask is gently agitated over a 45° C. water bath to dissolve the steric stabilizer and then attached to a rotary evaporator to remove the ethanol. Evaporation is accomplished under vacuum, keeping the sample flask in a water bath at 35°-50° C. Evaporation is continued until 101-103% of the theoretical weight of the ethanol has been removed (note: excess loss is due to removal of either some water of hydration or propylene glycol from the aluminum chlorohydrex PG), resulting in the formation of the adduct.

For precipitation of the adduct from an aqueous solution, a 25-30% aqueous solution of the antiperspirant salt and steric stabilizer is used, with the water being removed either by rotary evaporation, as described above, or by lyophilization (freeze drying). For lyophilization, the lyophilization flask is filled to no more than 40% of its total volume with the aqueous solution. The solution is then frozen as a shell, covering the inside surface of the flask, by rotating the flask in a dry ice-acetone bath. The frozen solution is then lyophilized with no external heating for 18-24 hours.

The adduct and the appropriate amount of the carrier are transferred to an Oster glass mixing jar and blended with an Osterizer TM for a total of 20 minutes. This results in the formation of an opaque dispersion. The opaque dispersion is treated with the proper amount of water in an intensive mixing machine, such as a Vortex Genie, for about 10 minutes to develop transparency. The clarity of the dispersion can be described according to the following rating scale.

CLARITY RATING SCALE

The following scale is based solely on visual appearance and is, therefore, subject to variability depending upon the observer.

| Rating | Description |
| --- | --- |
| 1 | Opaque |
| 2 | Opaque-to-translucent |
| 3 | Translucent |
| 4 | Translucent-to-clear (or slightly hazy) |
| 5 | Clear |

EXAMPLES 1-27

EXAMPLE 1

The following materials were treated according to the general procedure described above:

Oleth-10/Rehydrol II TM (1.5/1 w/w) in 190 proof ethanol was employed to give adduct I. This adduct was dispersed into isopropyl palmitate (IPP) at a concentration of 25% solids, which is equivalent to 10% active AP aluminum chlorohydrex PG (ACH-PG) and 15% Oleth-10. To obtain a dispersion of substantial clarity (4 on the Clarity Scale), it was necessary to incorporate 3 parts of water per 100 parts of dispersion.

EXAMPLE 2

Adduct I of Example 1 was used to make a dispersion at 40% solids, equivalent to 16% active AP ACH-PG, in IPP. Five percent water was added to give a dispersion with clarity=5.

EXAMPLE 3

Adduct I of Example 1 was used to make a dispersion at 50% solids, equivalent to 20% active AP ACH-PG in IPP. Three percent water was added to give a dispersion with clarity=5.

EXAMPLE 4

Adduct I of Example 1 was used to make a dispersion at 75% solids, equivalent to 30% active AP ACH-PG in IPP. Three percent water was added to give a dispersion with clarity=5.

EXAMPLE 5

Adduct I of Example 1 was dispersed into IPP/cyclomethicone (3/1 by volume) at 50% solids equivalent to 20% active AP ACH-PG. Three percent water was added to give a dispersion with clarity=5 (cyclomethicone is a volatile silicone commonly used in non-aqueous antiperspirants and other cosmetic systems).

EXAMPLE 6

Adduct I of Example 1 was dispersed into IPP/cyclomethicone (1/1 by volume) at 50% solids equivalent to 20% active AP ACH-PG. Three percent water was added to give a dispersion with clarity=5.

EXAMPLE 7

Adduct I of Example 1 was treated with 6 parts of water per 100 parts of adduct by blending in an Osterizer TM until homogeneous to give a hydrated adduct. This hydrated adduct was dispersed into IPP at a concentration of 50%, which is equivalent to approximately 20% ACH-PG, to give a dispersion with clarity=5.

EXAMPLE 8

Oleth-10/Rehydrol II TM (1.75/1 w/w) in 190 proof ethanol was employed to give an adduct II which when dispersed into IPP at 55% solids which is equivalent to 20% active AP ACH-PG gave a clear dispersion (clarity=5) when treated with 2.5% water.

EXAMPLE 9

Oleth-10/Rehydrol II TM (1.25/1 w/w) in 190 proof ethanol was employed to give an adduct III which when dispersed into IPP at 45% solids=20% ACH-PG gave a substantially clear dispersion (clarity=4) when treated with 3% water.

EXAMPLE 10

Adduct III of Example 9 was dispersed into IPP at 56% solids=25% ACH-PG to give a clear dispersion (clarity=5) when treated with 4% water.

EXAMPLE 11

Oleth-10/Rehydrol II TM (1/1 w/w) in 190 proof ethanol was employed to give an adduct IV which when dispersed into IPP at 40% solids=20% ACH-PG gave a substantially clear dispersion (clarity=4) when treated with 4.5% water.

EXAMPLE 12

Adduct IV of Example 11 was used to make a dispersion at 50% solids, equivalent to 25% active AP ACH-PG, in IPP. Seven percent water was added to give a dispersion with clarity=5.

EXAMPLE 13

Adduct IV of Example 11 was used to make a dispersion at 60% solids, equivalent to 30% active AP ACH- PG, in IPP. Seven percent water was added to give a dispersion with clarity=5.

EXAMPLE 14

Oleth-10/Rehydrol II ™ (0.5/1 w/w) in 190 proof ethanol was employed to give an adduct V which when dispersed in IPP at 30% solids=20% ACH-PG can be used in a variety of conventional non-aqueous dispersion or stick formulations to produce smooth compositions that, unlike current products, do not form a white chalky residue on the skin.

EXAMPLE 15

Oleth-20/Rehydrol II ™ (1.5/1 w/w) in 190 proof ethanol was employed to give an adduct VI which when dispersed into IPP at 50% solids=20% ACH-PG gave a clear dispersion (clarity=5) when treated with 5% water.

EXAMPLE 16

Oleth-5/Rehydrol II ™ (1.5/1 w/w) in 190 proof ethanol was employed to give an adduct VII which when dispersed into IPP at 50% solids=20% ACH-PG gave a clear dispersion (clarity=5) when treated with 5% water.

EXAMPLE 17

Ceteth-10/Rehydrol II ™ (1.5/1 w/w) in 190 proof ethanol was employed to give an adduct VIII which when dispersed into IPP at 40% solids=16% ACH-PG gave a substantially clear dispersion (clarity=4) when treated with 4% water.

EXAMPLE 18

Nonoxynol-8/Rehydrol II ™ (1.5/1 w/w) in 190 proof ethanol was employed to give an adduct IX which when dispersed into IPP at 50% solids=20% ACH-PG gave a clear dispersion (clarity=5) when treated with 4% water.

EXAMPLE 19

Sucrose stearate/Rehydrol II ™ (1.5/1 w/w) in 190 proof ethanol was employed to give an adduct X which when dispersed in IPP at 50% solids=20% ACH-PG can be used in a variety of conventional non-aqueous dispersion or stick formulations to produce smooth compositions that, unlike current products, do not form a white chalky residue on the skin.

EXAMPLE 20

Laureth-4/Rehydrol II ™ (1/1 w/w) in 190 proof ethanol was employed to give an adduct XI which when dispersed into IPP at 40% solids=20% ACH-PG gave an opaque-to-translucent dispersion (clarity=2) when treated with 6% water.

EXAMPLE 21

Laureth-4/steareth-20/Rehydrol II ™ (0.75/0.75/1 w/w/w) in 190 proof ethanol was employed to give an adduct XII which when dispersed into IPP at 50% solids=20% ACH-PG gave a substantially clear dispersion (clarity=4) when treated with 5% water.

EXAMPLE 22

Laureth-23/trideceth-3/Rehydrol II ™ (0.75/0.75/1 w/w/w) in 190 proof ethanol was employed to give an adduct XIII which when dispersed into IPP at 50% solids=20% ACH-PG gave a translucent dispersion (clarity=3) when treated with 5% water.

EXAMPLE 23

Oleth-10/aluminum zirconium tetrachlorohydrex PEG (1.5/1 w/w) in 190 proof ethanol was employed to give an adduct XIV which when dispersed into IPP at 50% solids=20% AP salt gave a clear dispersion (clarity=5) when treated with 4% water.

EXAMPLE 24

Oleth-10/Rehydrol II ™ (1.5/1 w/w) in water was employed to give an adduct XV via rotary evaporation which when dispersed into IPP at 50% solids=20% ACH-PG gave a clear dispersion (clarity=5) when treated with 5% water.

EXAMPLE 25

Oleth-10/aluminum chlorohydrate(ACH)/propylene glycol (1.5/1/0.33 w/w/w) in water was employed to give an adduct XVI via rotary evaporation which when dispersed into IPP at 42.5% solids=15% ACH gave a clear dispersion (clarity=5) when treated with 5% water.

EXAMPLE 26

Oleth-10/ACH (1.5/1 w/w) in water was employed to give an adduct XVII via rotary evaporation which when dispersed into IPP at 50% solids=20% ACH gave a substantially clear dispersion (clarity=4) when treated with 6% water.

EXAMPLE 27

Oleth-10/ACH/propylene glycol (1.5/0.75/0.25 w/w/w) in water was employed to give an adduct XVIII via lyophilization which when dispersed into IPP at 50% solids=15% ACH gave a substantially clear dispersion (clarity=4) when treated with 3% water.

To confirm that sub-micron size particles of ACH had been produced, transmission electron microscopy was performed on replicas of both the adduct and clear dispersion of Example 3. The resulting micrographs revealed the presence of approximately 0.05 micron particles that in many cases appear to have a 0.015 micron coating due to the steric stabilizer, Oleth-10.

Although the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A process for preparing a submicron antiperspirant adduct which comprises:
   (i) dissolving a mixture of an aluminum-containing antiperspirant salt and a steric stabilizer in a solvent;
   (ii) followed by precipitation of the antiperspirant salt into the steric stabilizer.

2. The process of claim 1 wherein the precipitation of the antiperspirant salt into the steric stabilizer is done by (a) evaporation, (b) freeze drying or (c) the addition of an agent to cause precipitation, followed by filtration to recover the adduct.

3. The process of claim 1 wherein the solvent is water or an alcohol.

4. The process of claim 3 wherein the alcohol is ethanol.

5. The process of claim 1 wherein the steric stabilizer is a nonionic surfactant.

6. The process of claim 5 wherein the surfactant is an ethoxylated alcohol, a polyethoxylated alcohol, an alkyl phenol ethoxylate, or a sucrose ester.

7. The process of claim 6 wherein the alcohol is a fatty alcohol having between 12 and 18 carbon atoms.

8. The process of claim 6 wherein the ethoxylated alcohol is stearyl, cetyl, or oleyl alcohol.

9. The process of claim 1 wherein the ratio of stabilizer to salt is about 0.1:1 to about 3:1.

10. The process of claim 1 wherein the ratio of stabilizer to salt is about 0.5:1 to about 3:1.

11. The process of claim 1 wherein the ratio of stabilizer to salt is about 0.75:1 to about 2.5:1.

12. The process of claim 11 wherein the ratio of stabilizer to salt is 1:1 to 2.25:1.

13. The process of claim 11 wherein the ratio of stabilizer to salt is 1.25:1 to 1.75:1.

14. The process of claim 1 wherein the aluminum-containing antiperspirant salt is an aluminum sulfate, an aluminum chloride, an aluminum sulfocarbolate, or an aluminum chlorohydrate.

15. The process of claim 1 wherein the aluminum-containing antiperspirant salt is an aluminum-zirconium salt.

16. An adduct prepared by the process of claim 1.

17. The adduct of claim 16 wherein substantially all of the adduct particles are less than about 0.4 microns.

18. The adduct of claim 16 wherein substantially all of the adduct particles are less than about 0.15 microns.

* * * * *